United States Patent
Webster et al.

(10) Patent No.: US 6,270,347 B1
(45) Date of Patent: Aug. 7, 2001

(54) NANOSTRUCTURED CERAMICS AND COMPOSITE MATERIALS FOR ORTHOPAEDIC-DENTAL IMPLANTS

(75) Inventors: Thomas J. Webster, Warminster, PA (US); Richard W. Siegel, Menands; Rena Bizios, Troy, both of NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 09/587,703

(22) Filed: Jun. 5, 2000

Related U.S. Application Data
(60) Provisional application No. 60/138,474, filed on Jun. 10, 1999.

(51) Int. Cl.[7] .................................................. A61C 8/00
(52) U.S. Cl. ........................................ 433/173; 433/201.1
(58) Field of Search ................................ 433/172, 173, 433/174, 175, 176, 201.1

(56) References Cited

U.S. PATENT DOCUMENTS
| | | | |
|---|---|---|---|
| 5,639,402 | * | 6/1997 | Barlow et al. ........................... 264/4 |
| 5,871,547 | * | 2/1999 | Abouaf et al. .......................... 623/22 |
| 6,013,591 | * | 1/2000 | Ying et al. .............................. 501/1 |

OTHER PUBLICATIONS

Webster, T.J., Siegel, R. W., Bizios, R. "Osteoblast Adhesion on Nanophase Alumina Substrates," Society for Biometrics Apr., 1998.

Webster, T.J. Siegel, R. W., Bixios, R. "Osteoblast Adhesion on Nanophase Alumina Substrates" Material Research Society Symposium, Apr., 1998.

Webster, T.J., Siegel, R. W., Bizios, R., "Osteoblast Adhesion on Nanophase Alumina," International Conference on Nanomaterials, Jun., 1998.

Webster, T.J., Siegel, R. W., Bizios, R., "Select Bone Cell Functions on Nanophase Alumina," Materials Research Society Symposium, Oct., 1998.

Webster, T.J., Siegel, R. W., Bizios, R., "Select Serum Proteins Mediate Osteoblast Adhesion on Nanophase Alumina," BMES, 1998.

Webster, T.J., Siegel, R. W., Bizios, R., "Mechanisms of Osteoblast Adhesion on Nanophase Alumina," AICHE, Nov. 1998.

Webster, T.J., Siegel, R. W., Bizios, R., "Nanophase Ceramics Enhance Select Bone Cell Functions," Society for Biomaterials, Apr., 1999.

Webster, T.J., Siegel, R. W., Bizios, R., An In Vitro Evaluation of Nanophase Alumia For Orthopaedic/Dental Applications, Bioceramics vol. 11, (Proceedings of the 11th International Symposium on Ceramics in Medicine), Ne York, NY, Nov., 1998.

* cited by examiner

*Primary Examiner*—Nicholas D. Lucchesi
(74) *Attorney, Agent, or Firm*—Heslin & Rothenberg, P.C.

(57) ABSTRACT

Methods for enhancing osteoblast functions on a surface of an orthopaedic/dental implant and enhancing osseointegration of an orthopaedic/dental implant consist of providing an orthopaedic/dental implant comprising one or more nanostructured ceramic having a grain size of 1–100 nm or a composite of one or more adhesion-promoting polymers and one or more nanostructured ceramic having a grain size of 1–100 nm, and placing the implant in the body of an animal, where it may be exposed to osteoblast cells. Alumina, titania, or hydroxyapatite is preferred as the nanostructured ceramic.

22 Claims, 11 Drawing Sheets

ENHANCED SELECT PROTEIN ADSORPTION ON NANOPHASE ALUMINA

▨ BOROSILICATE GLASS (REFERENCE MATERIAL); ☐ 167 nm GRAIN SIZE ALUMINA (CONNVENTIONAL), AND ▦ 24 nm GRAIN SIZE ALUMINA (NANOPHASE).

ENHANCED SELECT PROTEIN ADSORPTION ON NANOPHASE ALUMINA

▨ BOROSILICATE GLASS (REFERENCE MATERIAL); ☐ 167 nm GRAIN SIZE ALUMINA (CONNVENTIONAL), AND ▦ 24 nm GRAIN SIZE ALUMINA (NANOPHASE).

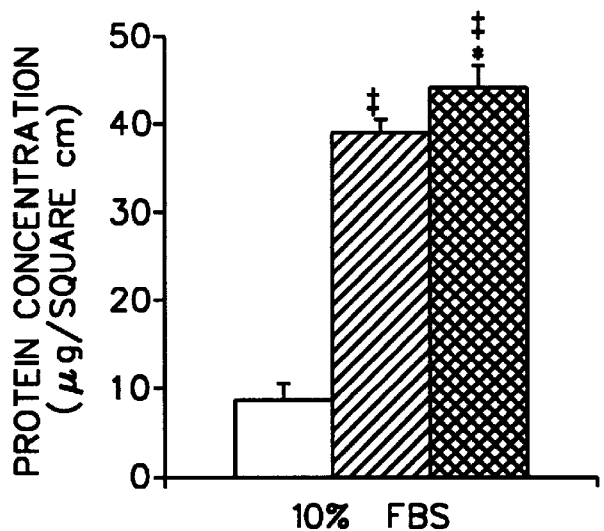

ENHANCED SELECT PROTEIN ADSORPTION ON NANOPHASE HYDROXYAPATITE

▨ BOROSILICATE GLASS (REFERENCE MATERIAL); ☐ 179 nm GRAIN SIZE HYDROXYAPATITE (CONNVENTIONAL), AND ▦ 67 nm GRAIN SIZE HYDROXYAPATITE (NANOPHASE).

*fig. 5A*

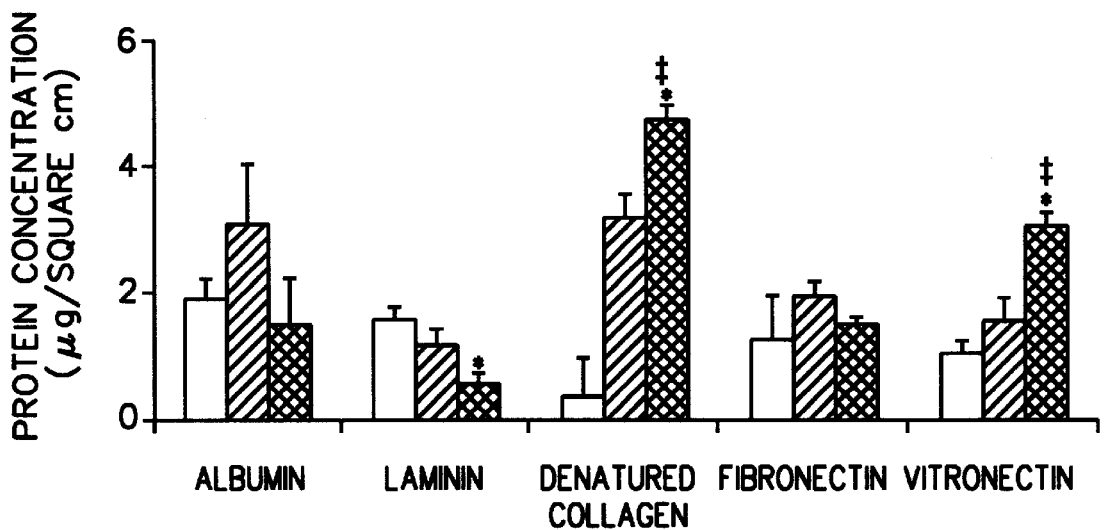

ENHANCED SELECT PROTEIN ADSORPTION ON NANOPHASE HYDROXYAPATITE

▨ BOROSILICATE GLASS (REFERENCE MATERIAL); ☐ 179 nm GRAIN SIZE HYDROXYAPATITE (CONNVENTIONAL), AND ▦ 67 nm GRAIN SIZE HYDROXYAPATITE (NANOPHASE).

*fig. 5B*

NANOSTRUCTURED CERAMICS AND COMPOSITE MATERIALS FOR ORTHOPAEDIC-DENTAL IMPLANTS

This application claim benefit to Provisional application No. 06/138,474 filed Jun. 10, 1999.

FIELD OF THE INVENTION

The invention relates to implants composed of nanostructured ceramics.

BACKGROUND OF THE INVENTION

Materials conventionally utilized in implants for orthopaedic and/or dental applications have included commercially pure titanium, Ti—6Al—4V and Co—Cr—Mo alloys. These have generally been selected based on mechanical properties, primarily strength under loading. Unfortunately, the use of conventional metals and metal alloys that meet mechanical requirements for bone replacements can result in metal material failure under long-term physiological loading, necessitating the surgical removal of failed bone implants.

Traditional ceramics have long been appreciated for their cytocompatibility. Conventional ceramic formulations of materials such as hydroxyapatite, bioglasses, bioactive glass ceramics, and calcium phosphate have been shown to enhance formation of new bone mineralized matrix. ("Conventional" refers to ceramics having a grain size greater than 100 nm. In contrast, "nanostructured", "nanophase" and "nanomaterial" refer to ceramics having a grain size of less than 100 nm in at least one direction.) Mechanical properties, specifically, ductility and toughness, of these conventional biosubstitutes, however, are generally not comparable to natural bone. Consequently, use of these materials in orthopaedic/dental applications has been limited. As one example, alumina has been used in the treatment of hand and elbow fractures, edentations, and in arthroplasty. There is therefore a need for biomaterials having ductility and toughness comparable to natural bone.

Implants composed of conventional ceramics have also experienced clinical failure. The cause of failure in the case of ceramic implants has been attributed to a lack of direct bonding with bone, that is, insufficient osseointegration. Osseointegration is necessary in order to stabilize orthopaedic/dental prostheses in situ, to minimize motion-induced damage to surrounding tissues, and to increase overall implant efficacy. Insufficient bonding of juxtaposed bone to an orthopaedic/dental implant can be caused by material surface properties that do not support new bone growth, as with implant materials composed of metal or conventional ceramics. The extent of osseointegration between bone and a newly implanted material is influenced by many factors including a number of host tissue responses. Physical and chemical properties of the biomaterial surface control the type and magnitude of cellular and molecular events at the tissue-implant interface.

Adhesion of bone-forming cells, or osteoblasts, to an implant is initially required for osseointegration. However, enhanced adhesion of osteoblasts to material surfaces does not necessarily result in enhancement of the long-term cell functions which lead to osseointegration of orthopaedic/dental implants and, therefore, a successful implant. For example, Dee, et al. immobilized RGDS (Arginine-Glycine-Aspartic Acid-Serine) peptides on glass [*Biomaterials*, 17 (2): pages 209–15 (1996)]. They observed enhanced osteoblast adhesion but not enhancement of subsequent functions, finding that mineralization on the peptide-modified glass was similar to that on unmodified glass. Osteoblast functions which occur subsequent to adhesion, and which are required for an effective implant, include proliferation, alkaline phosphatase synthesis, and deposition of extracellular matrix calcium. Enhancement of these long-term osteoblast functions on nanophase ceramics has not been reported. Therefore, there is a need for biomaterials having surface properties that enhance these and other long-term osteoblast functions. There is also a need for biomaterials with surface properties that would aid in the formation of new bone at the tissue/biomaterial interface and therefore, improve orthopaedic/dental implant efficacy.

SUMMARY OF THE INVENTION

It has been unexpectedly discovered that incorporating nanostructured ceramics in an orthopaedic/dental implant can enhance long-term osteobtast functions on the surface of that implant; osseointegration of the implant is also enhanced. The term "implant" as used herein includes grafts, fillers and cements. Accordingly, in one aspect, the present invention relates to a method for enhancing osteoblast functions on a surface of an orthopaedic/dental implant comprising providing an orthopaedic/dental implant comprising one or more nanostructured ceramic having a grain size of 1–100 nm or a composite of one or more adhesion-promoting polymers and one or more nanostructured ceramic having a grain size of 1–100 nm, and exposing the implant to osteoblast cells. The nanostructured ceramic is preferably chosen from alumina, titania, and hydroxyapatite. In another aspect, the present invention relates to a method for enhancing osseointegration of an orthopaedic/dental implant comprising providing an implant comprising one or more nanostructured ceramic having a grain size of 1–100 nm or a composite of one or more adhesion-promoting polymers and one or more nanostructured ceramic having a grain size of 1–100 nm, and placing the implant in an animal.

In yet another aspect, the present invention relates to an orthopaedic/dental implant comprising one or more nanostructured ceramic having a grain size of 1–100 nm. The nanostructured ceramic is preferably chosen from alumina, titania, and hydroxyapatite. The grain size of the nanostructured ceramic is preferably about 30–70 nm; for alumina, grain size is preferably about 49–67 nm, and for titania, grain size is preferably about 32–56 nm. The implant may also comprise a substrate coated with one or more nanostructured ceramic.

In another aspect, the present invention relates to an orthopaedic/dental implant comprising a nanocomposite of one or more nanostructured ceramic having a grain size of 1–100 nm and at least one of an adhesion-promoting peptide and a non-peptide polymer. The adhesion-promoting polymer is preferably a peptide incorporating a KRSR or an RGD sequence; the non-peptide polymer is preferably polylactic acid. The implant may also comprise a substrate coated with a nanocomposite.

BRIEF DESCRIPTION OF THE DRAWINGS

FIG. 5 is a graph showing enhanced adsorption of select proteins on nanophase hydroxyapatite in comparison with adsorption on conventional hydroxyapatite and a borosilicate glass reference.

DETAILED DESCRIPTION OF THE INVENTION

Figure 1:
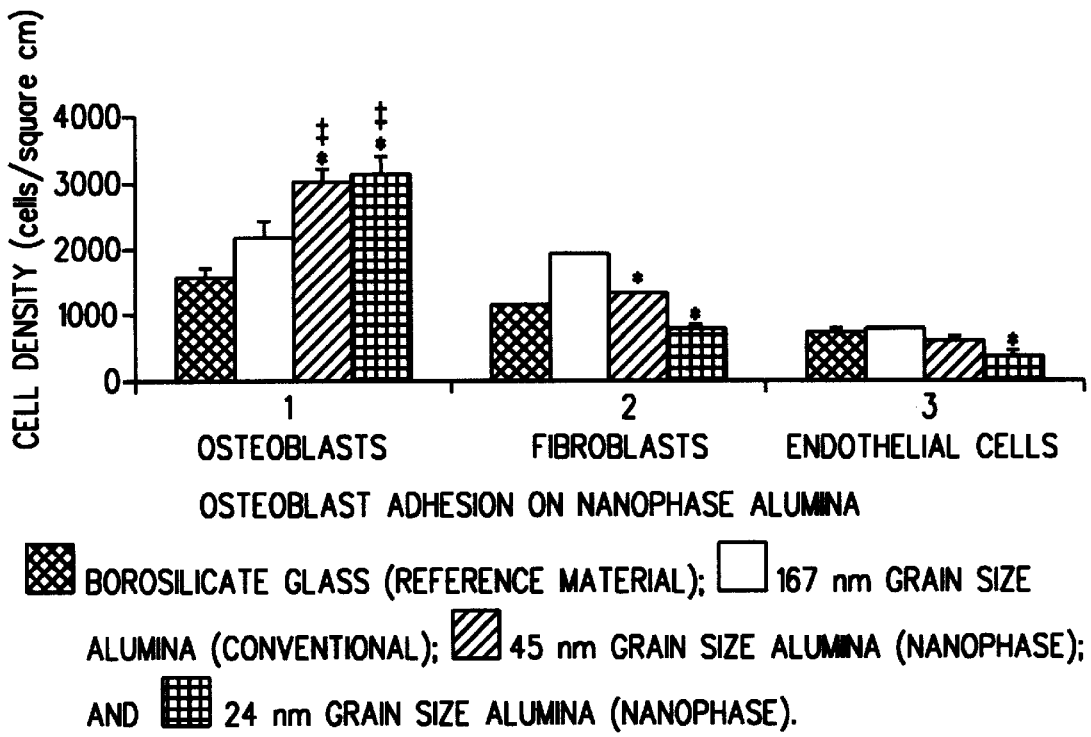
FIG. 1 is a graph showing adhesion of osteoblast, fibroblast and endothelial cells to conventional and nanophase alumina in comparison with adhesion to a borosilicate glass reference.

An orthopaedic/dental implant according to the present invention comprises one or more nanostructured ceramic having a grain size of 1–100 nm. The nanostructured ceramic is preferably composed of alumina, titania, or hydroxyapatite. Preferably, the grain size ranges from about 30–70 nm. For nanostructured alumina, the preferred grain size range is about 49–67 nm; for nanostructured titania, the preferred grain size range is about 32–56 nm.

A bone or dental implant may be manufactured using a ceramic having a grain size in the 1–100 nm range as a starting material. Nanophase alumina and titania are commercially available from several sources, including Nanophase Technologies Corporation. Nanophase Technologies Corporation supplies alumina having a grain size of 23 nm, as well as titania having a grain size of 32 nm. Both of these are particularly suitable as a raw material for the orthopaedic/dental implant of the present invention. Methods of fabricating a ceramic part suitable for use as an implant are well known in the art. Likewise, methods of producing a ceramic having a desired grain from a particular powdered starting material having a grain size in the nanometer range are also known. Generally, where the starting material is in the form of a powder, the powder is compressed and then heated to a temperature sufficiently high, and for a period sufficiently long to sinter grain sizes to less than 100 nm. The temperature and time will vary according to the raw materials used, and the desired final grain size. For example, alumina powder was sintered at various temperatures for two hours. The starting grain size of the powder was 23 nm. After sintering for two hours at 1000° C., 1100° C., and 1200° C., the average grain size of the as-pressed alumina compacts increased to 24 nm, 45 nm, and 167 nm, respectively. Known wet chemical methods may be used to produce hydroxyapatite having a grain size in the nanometer range. The material may be prepared in aqueous solution and precipitated from solution with stirring. The temperature of the solution during the precipitation and the time period over which the precipitation is carried out affect the grain size of the precipitate. For example, precipitation at room temperature for 24 hours produced hydroxyapatite having a grain size of 67 nm. Precipitation at 90° C. for three hours produced a material having a grain size of 167 nm. It can be seen from the these examples that particular conditions required to produce a desired result may be readily determined without extensive experimentation.

Bone and/or dental implants composed of nanostructured ceramics according to the present invention typically have surface properties that are significantly different than those composed of conventional materials. For example, wettability by aqueous solutions, as measured by contact angle, is significantly greater (lower contact angle) for nanostructured materials than for conventional materials. Increased wettability suggests that the surface of nanostructured materials has greater affinity for select protein absorption and subsequent osteoblast adhesion. Results of contact angle measurements of alumina and titania substrates of various grain sizes as shown in Table 1.

TABLE 1

| Material | Grain Size (nm) | Contact Angle (deg) |
|---|---|---|
| Reference: Borosilicate glass | NA | 17.3 ± 1.1 |
| Alumina | 177 | 18.6 ± 0.9 |
|  | 49 | 10.8 ± 1.3 |
|  | 23 | 6.4 ± 0.7 |
| Titania | 2120 | 26.8 ± 2.8 |
|  | 97 | 18.1 ± 3.2 |
|  | 32 | 2.2 ± 0.1 |

In addition, the surface roughness and surface area of implants composed of nanostructured materials is higher than that of implants composed of conventional materials. Table 2 shows that nanophase alumina and titania typically have higher surface area and greater surface roughness than comparable materials of conventional grain size. These surface properties may be determined by atomic force microscopy; an instrument such as an Autoprobe CP Atomic Force Microscope used in conjuction with image analysis software (Pro-scan) can generate micrographs and yield a quantitative measurement of surface roughness and surface area.

TABLE 2

|  | Alumina | | Titania | |
|---|---|---|---|---|
| Grain size, nm | 177 | 23 | 2120 | 32 |
| Surface Roughness, nm | 17 | 20 | 16 | 32 |
| Surface area, $\mu m^2$ | 1.15 | 1.73 | 1.07 | 1.45 |

Mechanical properties of nanostructured ceramics are improved over conventional materials. Specifically, nanophase materials exhibit increased ductility and are consequently less brittle as grain size is reduced. For example, the modulus of elasticity of a 23 nm alumina sample was 70% lower than a sample having a conventional grain size of 177 nm. In this way, nanophase alumina possesses modulus of elasticity values close to those found in bone.

Cytocompatibility of implants composed of nanostructured ceramics is typically very good. For example, rat calvaria osteoblasts adherent on 23 nm grain size alumina exhibited a well-spread cell morphology, which is indicative of increased cellular interaction with a material surface. In contrast, there were mostly rounded, i.e., smaller and not spread osteoblasts adherent on alumina of grain size 177 nm. Osteoblast adhesion on the 23 nm grain size alumina was also significantly greater than on borosilicate glass (reference substrate) after 1, 2, and 4 hours.

An orthopaedic/dental implant according to the present invention may include an adhesion-promoting peptide, if desired. Peptides that promote adhesion between osteoblasts and a substrate, for example, integrin-binding peptides containing the Arginine-Glycine-Aspartic Acid (RGD) sequence [Puleo and Bizios, *Bone* 12, 271–276 (1991)], are known. Published PCT application WO 97/25999, entitled "Peptides for Altering Osteoblast Adhesion," describes specific peptides, including peptides incorporating the sequence KRSR, for enhancement of adhesion to substrates. Adhesion-promoting materials are typically used by attaching the peptide to the surface of a substrate to which adhesion is desired. WO 97/25999 teaches a technique for immobilizing peptides on the surface of a substrate by a silanization reaction. Substrates include conventional orthopaedic and dental implants composed of titanium metal. This technique or others known in the art may be used to immobilize adhesion-promoting peptides on the surface of implants composed of nanophase alumina, titania or hydroxyapatite.

An orthopaedic/dental implant according to the present invention may be a composite material termed herein a "nanocomposite", incorporating one or more natural or synthetic polymers, other than a peptide, in addition to the nanophase materials. For example, polylactic acid may be combined with nanophase materials to produce a composite having excellent mechanical properties while maintaining the enhanced adhesion of osteoblasts to the materials obtainable with nanophase materials alone. These nanocomposite materials may also include an adhesion-promoting peptide.

The nanocomposite materials preferably comprise about 50–99 parts by weight of a non-peptide polymer and about 1–50 parts by weight nanostructured ceramic, and more preferably about 30–99 parts by weight of a non-peptide polymer and about 1–30 parts by weight nanostructured ceramic. The non-peptide polymer is typically cytocompatible and is preferably bioabsorbable and/or bioerodable. It is also non-toxic, non-carcinogenic, and causes no adverse immunologic response. Representative useful materials include: polyfumarates; polylactides; polyglycolides; polycaprolactones; polyanhydrides; pyrollidones, for example, methylpyrollidone; cellulosic polymers; for example, carboxymethyl cellulose; methacrylates; collagens, for example, gelatin; glycerin and polylactic acid. Synthetic polymer resins may also be used, including, for example, epoxy resins, polycarbonates, silicones, polyesters, polyethers, polyolefins, synthetic rubbers, polyurethanes, nylons, polyvinylaromatics, acrylics, polyamides, polyimides, phenolics, polyvinylhalides, polyphenylene oxide, polyketones and copolymers and blends thereof. Copolymers include both random and block copolymers. Polyolefin resins include polybutylene, polypropylene and polyethylene, such as low density polyethylene, medium density polyethylene, high density polyethylene, and ethylene copolymers; polyvinylhalide resins include polyvinyl chloride polymers and copolymers and polyvinylidene chloride polymers and copolymers, fluoropolymers; polyvinylaromatic resins include polystyrene polymers and copolymers and poly α-methylstyrene polymers and copolymers; acrylate resins include polymers and copolymers of acrylate and methacrylate esters, polyamide resins include nylon 6, nylon 11, and nylon 12, as well as polyamide copolymers and blends thereof; polyester resins include polyalkylene terephthalates, such as polyethylene terephthalate and polybutylene terephthalate, as well as polyester copolymers; synthetic rubbers include styrene-butadiene and acrylonitrile-butadiene-styrene copolymers and; polyketones include polyetherketones and polyetheretherketones. The polymer is preferably polylactic acid.

Enhancement of long-term osteoblast functions, subsequent to adhesion of osteoblast to material surfaces, is required for long-term osseointegration of orthopaedic/dental implants. Such functions include osteoblast proliferation, alkaline phosphatase synthesis and deposition of extracellular matrix calcium on the implant. It has been unexpectedly found that manufacturing an orthopaedic/dental implant from a nanostructured ceramic or a polymer/ceramic composite, and exposing the implant to osteoblast cells leads to enhancement of long-term functions and osseointegration of the implant, as demonstrated in the following examples.

EXAMPLES

Example 1

Hydroxyapatite Preparation

At room temperature, calcium phosphate was added over a five minute interval to ammonium hydroxide:distilled water (1:5 v:v) and stirred for 24 hours. Hydroxyapatite (HA; $Ca_5(PO_4)_3(OH)$) precipitates were formed during this period; three different grain sizes were obtained by stirring the calcium nitrate:ammonium hydroxide:water solution under different conditions:

for 67 nm grain size—room temperature for 24 hours for 132 nm grain size—90° C. for 1 hour for 179 nm grain size—90° C. for 3 hours Each HA-containing solution was then centrifuged, filtered, dried at 60° C. for 8 hours, heated in air at 10° C./minute from room temperature to a final temperature of 1100° C., and sintered at 1100° C. for 60 minutes.

Examples 2–3

Cell Adhesion

Example 2

Adhesion of Osteoblasts, Fibroblasts, and Endothelial Cells

Osteoblasts were isolated via sequential collagenase digestion of neonatal rat calvaria according to established protocols and cultured in Dulbecco's Modified Eagle Medium (DMEM), supplemented with 10% fetal bovine serum in a 37° C., humidified, 5% $CO_2$/95% air environment. The osteoblastic phenotype of the cells was determined by alkaline phosphatase activity and formation of calcium containing mineral deposits in the extracellular matrix. Osteoblasts at population numbers 2–4 were used in the experiments.

Rat skin fibroblasts (cell line CRL-1231) were purchased from the American Type Culture Collection (ATCC; Rockville, Md.), characterized by the ATCC, and used at population numbers 10–15 in the experiments. Bovine arterial endothelial cells were isolated and characterized as reported in the literature (Polacek D, Lai R, Volin M V, Davies P F, *Am. J. of Path.*, 1993; 142(2):593–606); these cells were used at population numbers 20–25 in the experiments.

Osteoblasts, fibroblasts, and endothelial cells (3,500 cells/cm$^2$) in DMEM (either in the presence or absence of 10% fetal bovine serum) were separately seeded per substrate and allowed to adhere in a 37° C., humidified, 5% $CO_2$/95% air environment for 4 hours. At the end of the prescribed time period, non-adherent cells were removed by rinsing in phosphate buffered saline. Adherent cells on the opaque ceramic substrates were fixed in situ with 4% formaldehyde in sodium phosphate buffer; the cell nuclei were stained with Hoechst (No. 33342; Σ), visualized and counted using fluorescence (365 nm excitation; 400 nm emission) microscopy with Image Pro image analysis software. Cells adherent on glass (reference substrate) were fixed in situ with 4% formaldehyde in sodium phosphate buffer and stained with Commassie Brilliant Blue (Σ); these cells were, thus, visualized and counted using a light microscope.

Cell density (cells/cm$^2$) was determined by averaging the number of adherent cells in five random fields per substrate. Each cell adhesion experiment was run in triplicate and repeated at three separate times.

In order to elucidate the role of protein type and concentration in mediating select, enhanced osteoblast adhesion on nanophase ceramics, substrates of interest to the present study were pretreated with various concentrations (0.0005, 0.005, 0.05, 0.5 and 5 μg/mL phosphate buffered saline) of either albumin, laminin, denatured collagen, fibronectin, or vitronectin in a sterile environment, at room temperature, for 24 hours. Control samples were maintained in Dulbecco's Modified Eagle Medium (DMEM), supplemented with 10% fetal bovine serum, in a sterile environment, at room temperature for 24 hours. After the prescribed time period, each substrate was gently rinsed with phosphate buffered saline at room temperature and used immediately in cell culture experiments as described above.

Figure 2:
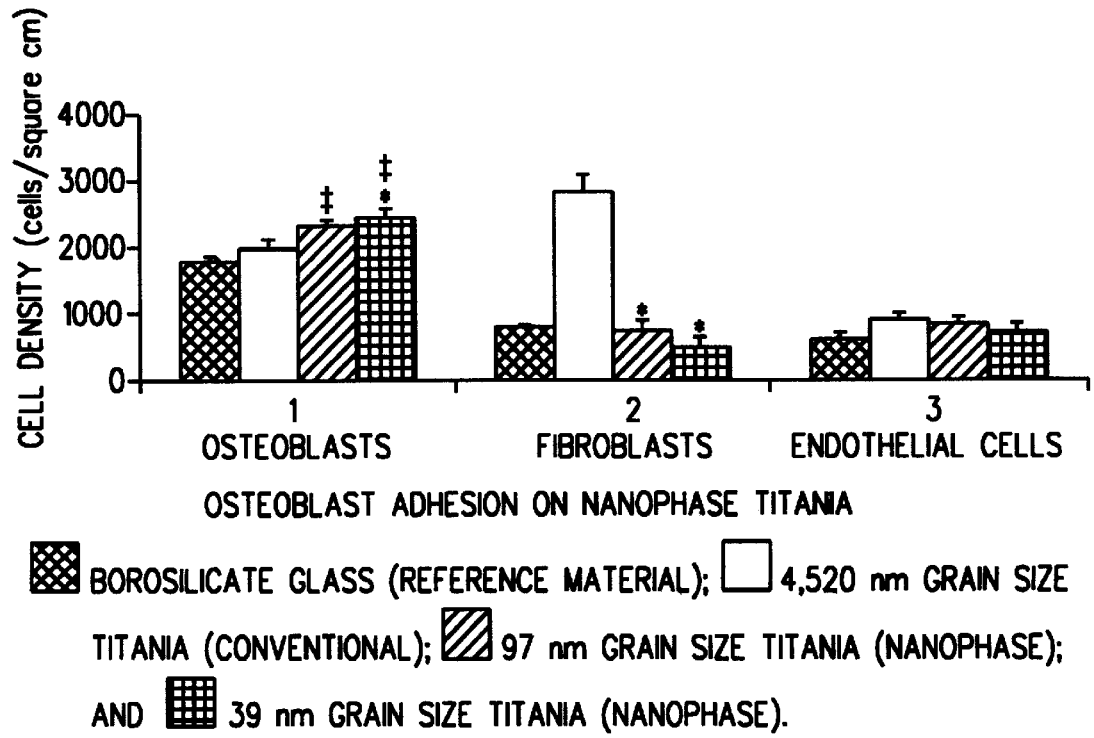
FIG. 2 is a graph showing adhesion of osteoblast, fibroblast and endothelial cells to conventional and nanophase titania in comparison with adhesion to a borosilicate glass reference.
Figure 3:
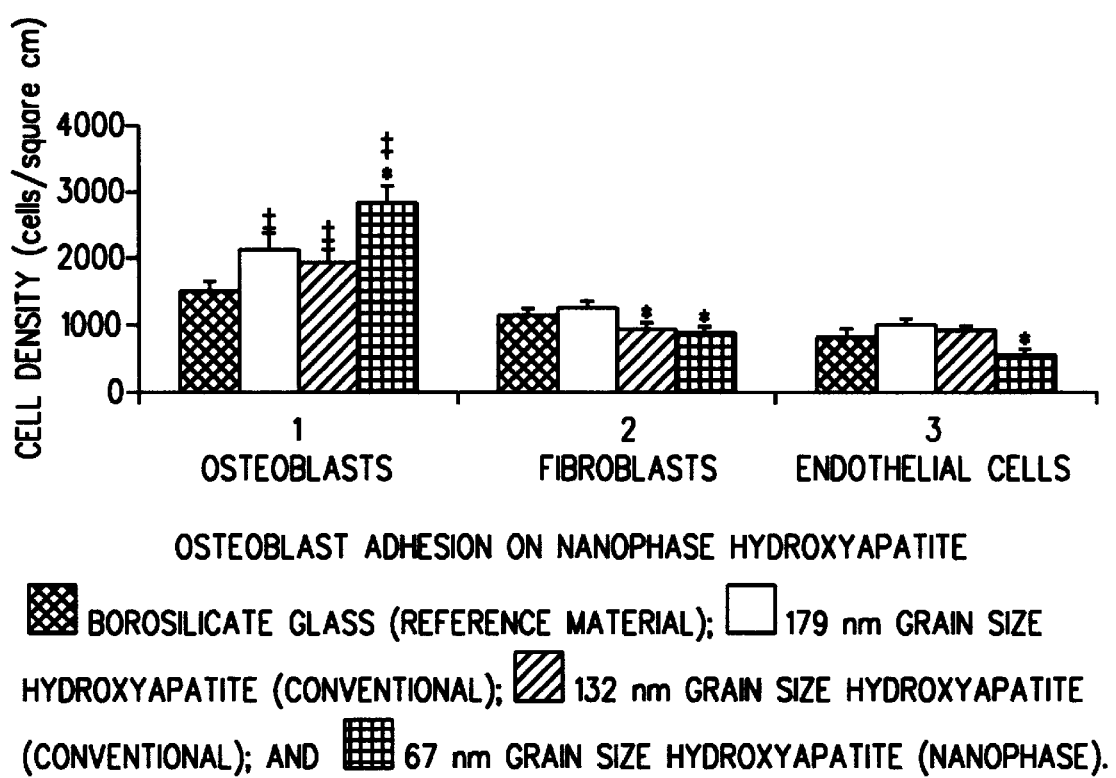
FIG. 3 is a graph showing adhesion of osteoblast, fibroblast and endothelial cells to conventional and nanophase hydroxyapatite in comparison with adhesion to a borosilicate glass reference.

In the absence of serum, osteoblast adhesion was similar on all substrates investigated. In contrast, in the presence of serum, osteoblast adhesion was significantly greater on nanophase (24 nm alumina, 39 nm titania, and 67 nm HA) than on conventional (167 nm alumina, 4,520 nm titania, and 179 nm HA) ceramics after 4 hours (FIGS. 1, 2, and 3). In contrast to enhanced osteoblast adhesion on nanophase ceramics, fibroblast adhesion was significantly less on nanophase (24 and 45 nm alumina, 39 and 97 nm titania, and 67 nm HA) than on conventional ceramics after 4 hours (FIGS. 1, 2, and 3). Compared to adhesion on conventional alumina and titania, endothelial cell adhesion was significantly less on the nanophase (24 nm alumina and 39 nm titania) formulations of these ceramics; endothelial cell adhesion was similar on both nanophase and conventional HA (FIGS. 1, 2, and 3). Furthermore, compared to fibroblast and endothelial cell adhesion, osteoblast adhesion was more than three times greater on each (that is, alumina, titania, and HA) nanophase ceramic tested (FIGS. 1, 2, and 3).

Figure 4A:
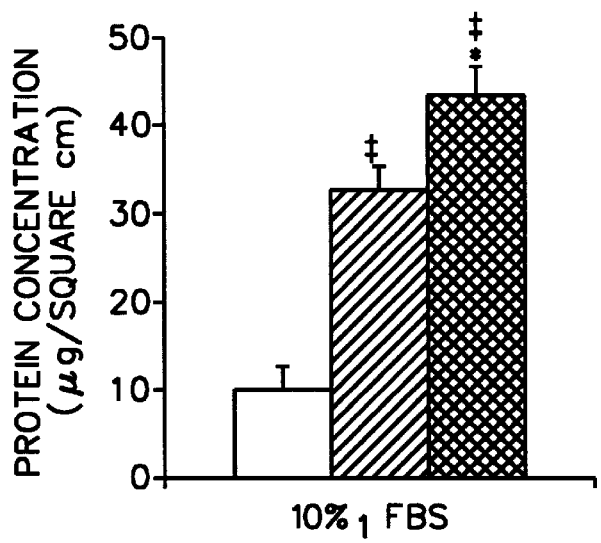
FIG. 4 is a graph showing enhanced adsorption of select proteins on nanophase alumina in comparison with adsorption on conventional alumina and a borosilicate glass reference.
Figure 4B:
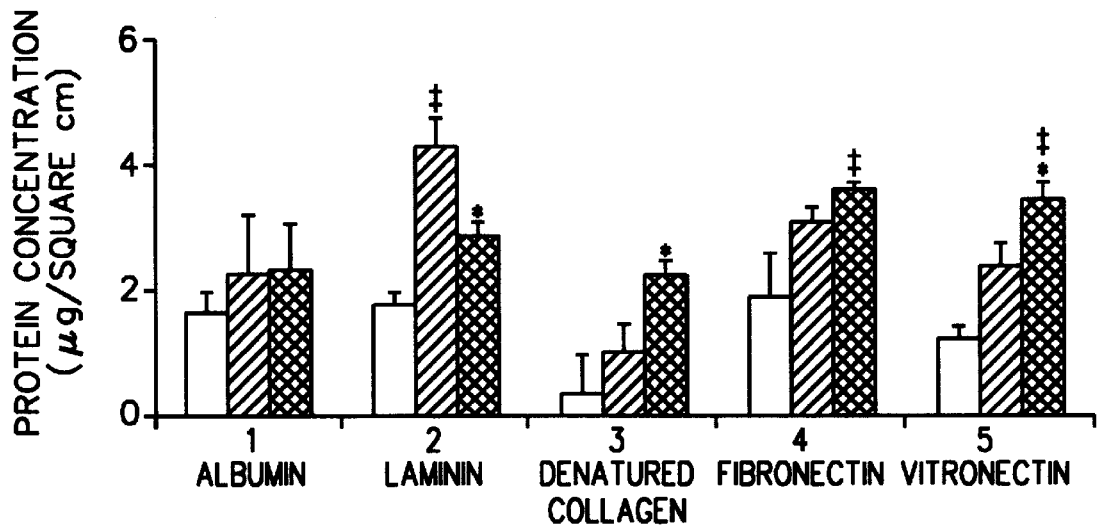

The type and concentration of proteins adsorbed on nanophase and conventional ceramics of interest to the present study was also investigated and compared. Compared to conventional alumina (167 nm) and HA (179 nm), a significantly (P<0.01) greater concentration of 10% fetal bovine serum, which contains unknown concentrations of numerous proteins including albumin, laminin, collagen, fibronectin and vitronectin, adsorbed onto the nanophase alumina (24 nm) and HA (67 nm) after four hours (FIGS. 4 and 5). In fact, 17% and 11% more proteins contained in fetal bovine serum adsorbed per square centimeter on nanophase alumina and HA, respectively. Significantly (P<0.01) greater concentrations of vitronectin (a protein that has been shown to mediate osteoblast adhesion) and denatured collagen adsorbed on nanophase alumina and HA than on conventional formulations of the same ceramics. In contrast, and compared to respective nanophase ceramic formulations, significantly (P<0.01) greater amounts of laminin (a protein that has been shown to mediate endothelial cell adhesion) adsorbed on conventional alumina and HA. Adsorption of fibronectin and albumin were similar on nanophase and conventional alumina and HA, respectively.

Example 3

Osteoblast Adhesion: Effect of Grain Size: Alumina and Titania

Osteoblasts were enzymatically lifted from polystyrene tissue culture flasks using less than 1 mL of low-trypsin EDTA (Σ) before suspension in DMEM (in the presence or absence of 10% fetal bovine serum). Osteoblasts (3500 cells/cm$^2$) in DMEM (in the presence of 10% fetal bovine serum) were seeded per substrate and allowed to adhere in a 37° C., humidified, 5% $CO_2$/95% air environment for 0.5, 1, 2, and 4 h. After each prescribed time period, non-adherent osteoblasts were removed by rinsing in phosphate buffered saline. Osteoblasts adherent on opaque alumina and titania were fixed with 4% formaldehyde in sodium phosphate buffer and stained with Hoechst (No. 33342; Σ); the cell nuclei were, thus, visualized and counted in situ using fluorescence (365 nm excitation; 400 nm emission) microscopy with image analysis software (Image Pro).

Osteoblasts from different isolations of neonatal rat calvaria were used in this study; cells from one and the same batch, however, were used per experimental run. The adhesion experiments were run in triplicate and repeated at three different times per substrate type. Cell density (cells/cm$^2$) was determined by averaging the number of adherent cells in five random fields per substrate. Cell adhesion density was analyzed statistically using standard analysis of variance (ANOVA) techniques; statistical significance was considered at P<0.05.

Figure 6:
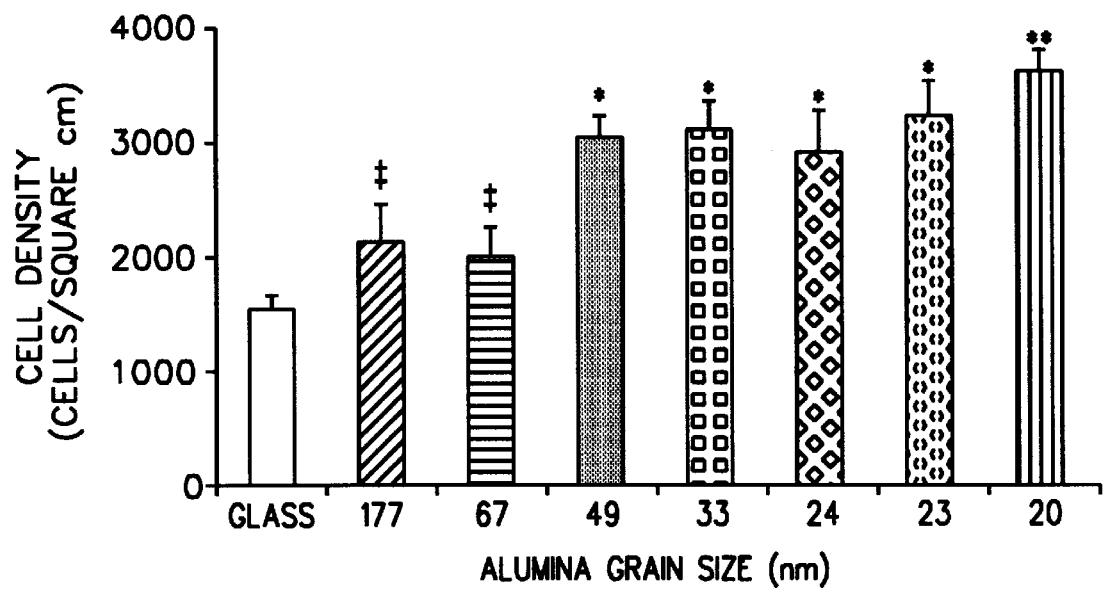
FIG. 6 is a graph showing adhesion of osteoblasts to alumina of various grain sizes in comparison with adhesion to a borosilicate glass reference.
Figure 7:
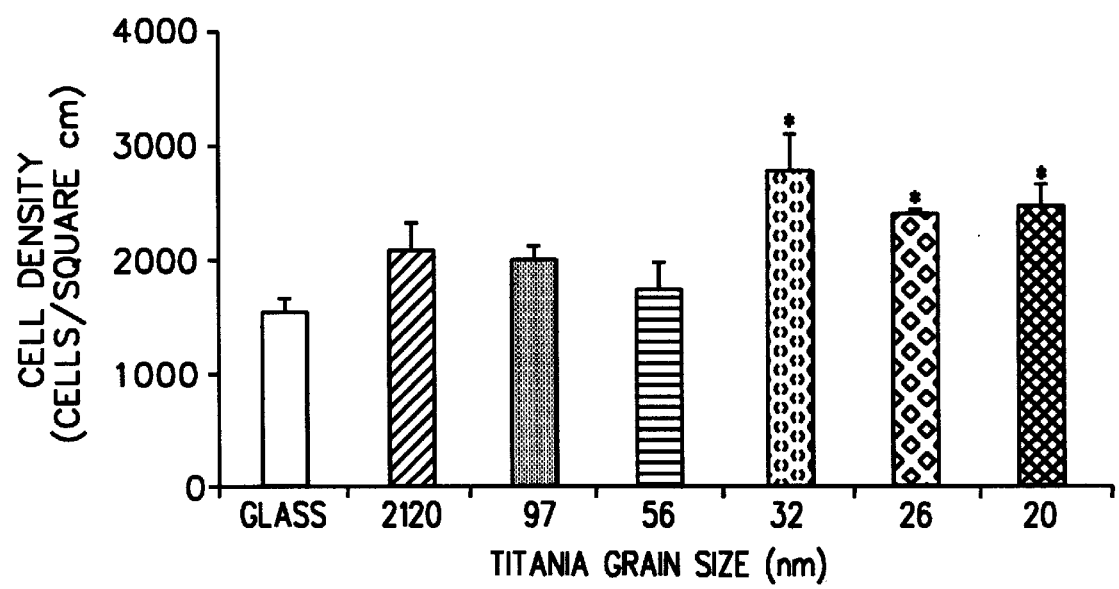
FIG. 7 is a graph showing adhesion of osteoblasts to titania of various grain sizes in comparison with adhesion to a borosilicate glass reference.

Osteoblast adhesion was significantly (P<0.01) greater on the 20 nm grain size nanophase alumina than on the 177 nm grain size conventional alumina after 4 h (FIG. 6); in fact, osteoblast adhesion was significantly (P<0.05) greater on alumina with grain sizes in the range of 23–49 nm than on alumina with grain sizes in the range of 67 and 177 nm. Moreover, the average ostoblast adhesion on alumina with grain sizes less than 49 nm was 52% greater than on alumina with grain sizes greater than 67 nm after 4 h (3125 versus 2050 cells/cm$^2$). Similarly, osteoblast adhesion was significantly (P<0.05) greater on titania with grain sizes in the range of 20–32 nm than on titania with grain sizes greater than 56–2.12 μm (FIG. 7). The average osteoblast adhesion on titania with grain sizes less than 32 nm was 24% greater than on titania with grain sizes greater than 56 nm after 4 h (2589 versus 11961 cells/cm$^2$). These results imply that there may be a preferred grain size (between 49 and 67 nm for alumina and between 32 and 56 nm for titania) in mediating osteoblast adhesion to nanophase ceramics.

Examples 4–6

Enhanced Long-Term Cell Functions

Example 4

Osteoblast Proliferation

Osteoblasts in DMEM (supplemented with 10% fetal bovine serum) were seeded (2,500 cells/cm$^2$) onto the substrates of interest to the present study. The cells were then cultured in DMEM (supplemented with 10% fetal bovine serum) under standard cell conditions for 1, 3, and 5 days. At the end of the prescribed time periods, osteoblasts were fixed in situ with 4% formaldehyde for 10 minutes. Osteoblasts cultured on opaque conventional (control substrates) and nanophase ceramics were stained with Hoechst (No. 33342; Σ) fluorescent dye; the cell nuclei were thus visualized and the number of cells in each of five random fields per substrate were counted using a fluorescence (365 nm excitation; 400 nm emission) microscope with image analysis software (Image Pro). Osteoblasts cultured on glass (reference substrate) were stained in situ with Commassie Brilliant Blue staining solution; adherent cells (on each of five random fields per substrate) were thus visualized and counted using a light microscope. The average cell count per substrate was expressed as "cell density" or cells/cm$^2$ of substrate surface area.

Figure 8A:
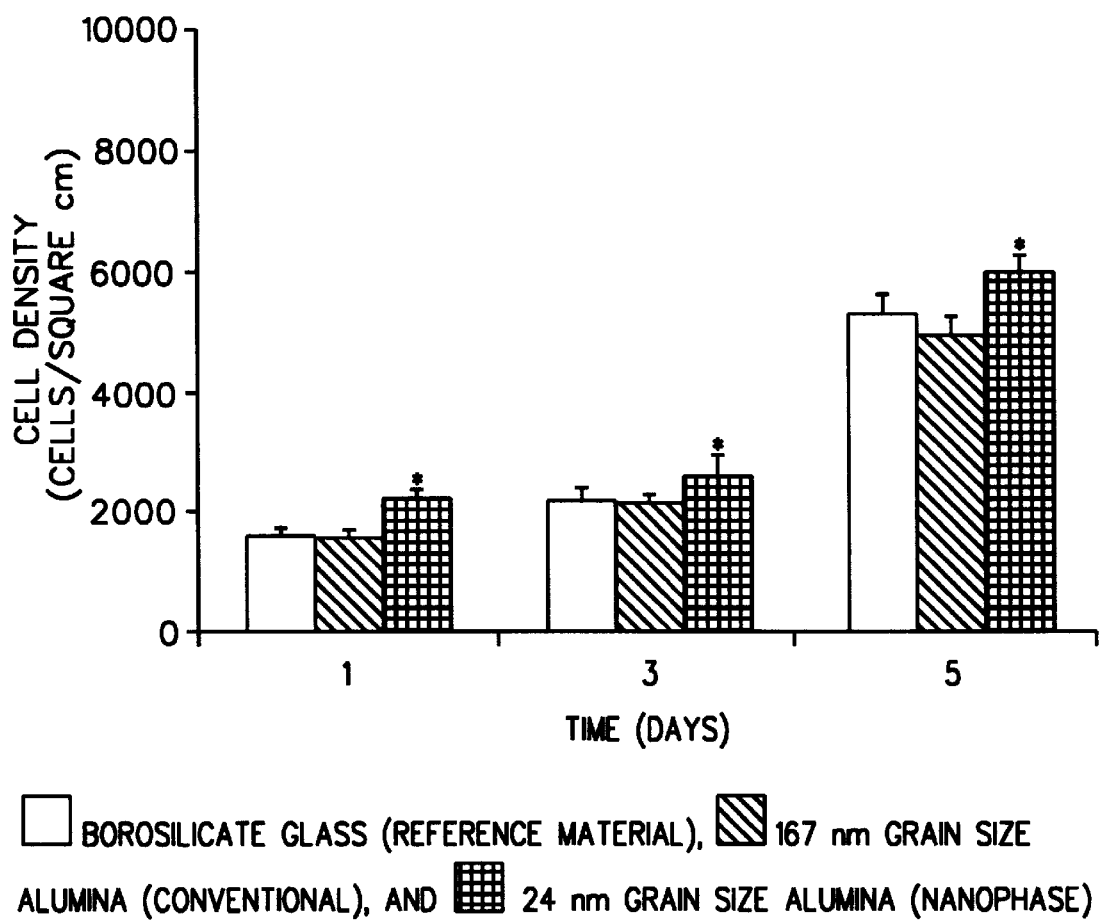
FIG. 8 is a graph showing proliferation of osteoblasts seeded on (a) conventional and nanophase alumina; (b) conventional and nanophase titania; and (c) conventional and nanophase hydroxyapatite, each in comparison with a borosilicate glass reference.
Figure 8B:
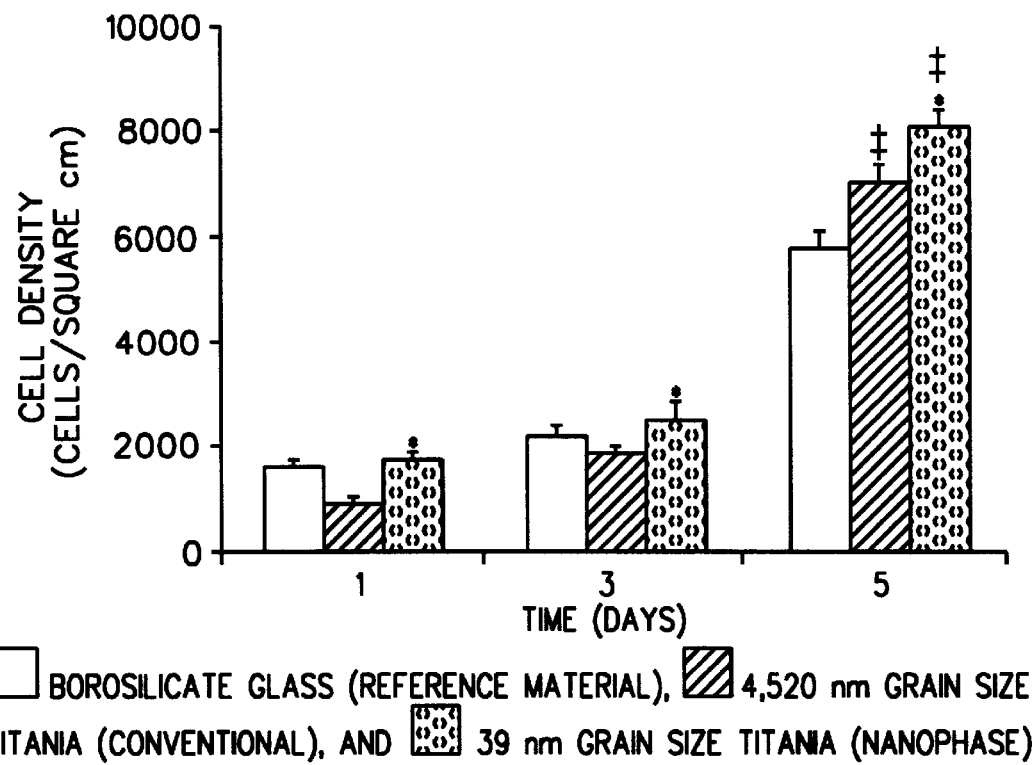
Figure 8C:
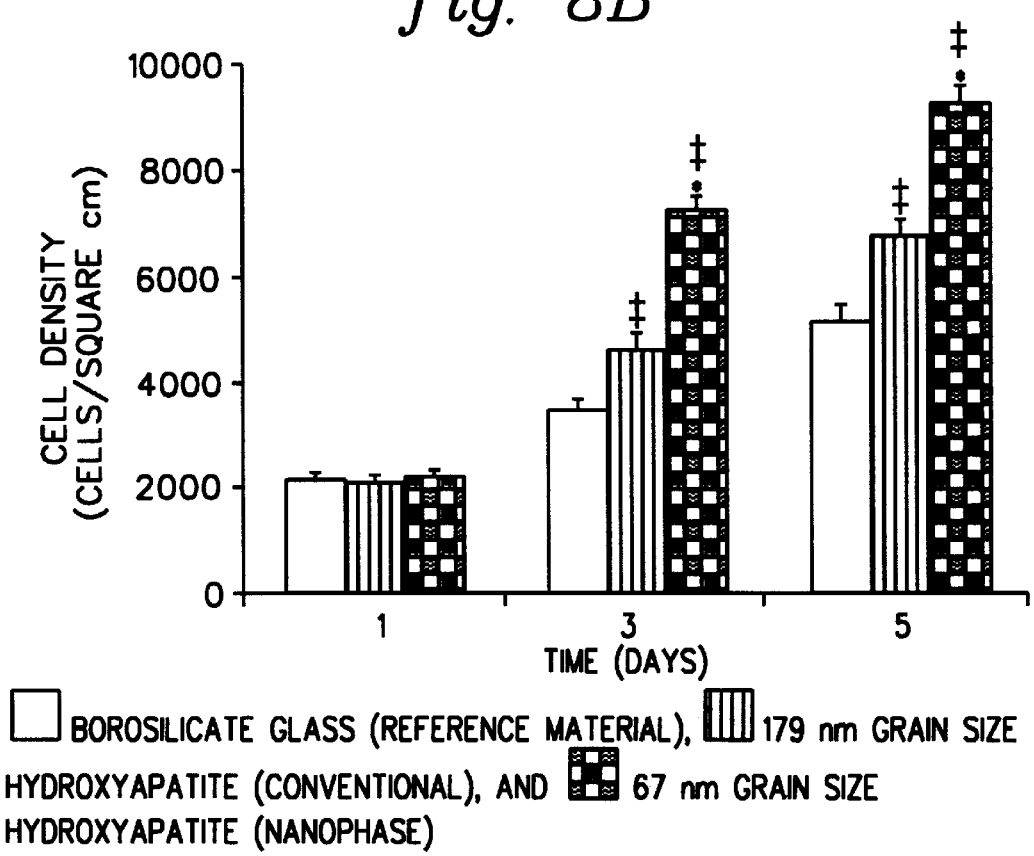

Compared to respective conventional formulations of the same ceramic and to borosilicate glass (reference substrate), osteoblast proliferation increased on all nanophase ceramics tested in the present study (FIGS. 8a, b, and c). Specifically, the proliferation of osteoblasts were significantly ($P<0.01$) greater on nanophase, than on conventional, alumina (FIG. 8a) and titania (FIG. 8b) after 1, 3, and 5 days of culture. Osteoblast proliferation was similar on nanophase and on conventional HA after 1 day of culture (FIG. 8c), but was significantly ($P<0.01$) greater on nanophase HA after 3 and 5 days of culture (FIG. 8c).

Example 5
Synthesis of Alkaline Phosphatase

Osteoblasts (40,000 cells/cm$^2$) were seeded onto the substrates of interest to the present study and cultured in DMEM (supplemented with 10% fetal bovine serum, 50 µG/mL L-ascorbate (Σ) and 10 mM β-glycerophosphate (Σ)) under standard cell culture conditions for 7, 14, 21, and 28 days. At the end of the prescribed time periods, osteoblasts were lysed using distilled water and three freeze-thaw cycles. Total protein content in the cell lysates was determined spectrophotometrically using a commercially available kit (Pierce Chemical Co.) following manufacturer's instructions. For this purpose, aliquots of each protein-containing, distilled-water supernatant were incubated with a solution of copper sulfate and bicinchoninic acid at 37° C. for 30 minutes. Light absorbance of these samples was measured at 570 nm on a MR600 Spectrophotometric Microplate reader (Dynatech). Total intracellular protein (expressed as mg) synthesized by osteoblasts cultured on the substrates of interest to the present study was determined from a standard curve of absorbance versus known concentrations of albumin run in parallel with experimental samples. Total intracellular protein synthesized by osteoblasts cultured on conventional ceramics served as controls.

The method of Lowry (1954) was used to assay alkaline phosphatase activity in the cell lysates. For this purpose, aliquots (100 µL) of the distilled water supernatant were incubated with 500 µL of reaction solution (containing 0.6 M 2-amino-2methyl-1-propanol (pH=10.0), and 10 mM p-nitrophenylphosphate) solution (Diagnostic Kit #104; Σ) at 37° for 30 minutes; the reaction of p-nitrophenol conversion to p-nitrophenylate was stopped by adding 1.5 mL of 0.25 N NaOH. Light adsorbance of these examples was measured on a spectrophotometer (MR600 Spectrophotometric Microplate Reader; Dynatech) at 400 nm. The alkaline phosphatase activity (expressed as nanomoles of converted p-nitrophenol/min) was normalized by total intracellular protein synthesis and expressed as nanomoles of converted p-nitrophenol/min/mg protein. Alkaline phosphatase activity of osteblasts cultured on conventional ceramics served as controls.

Figure 9A:
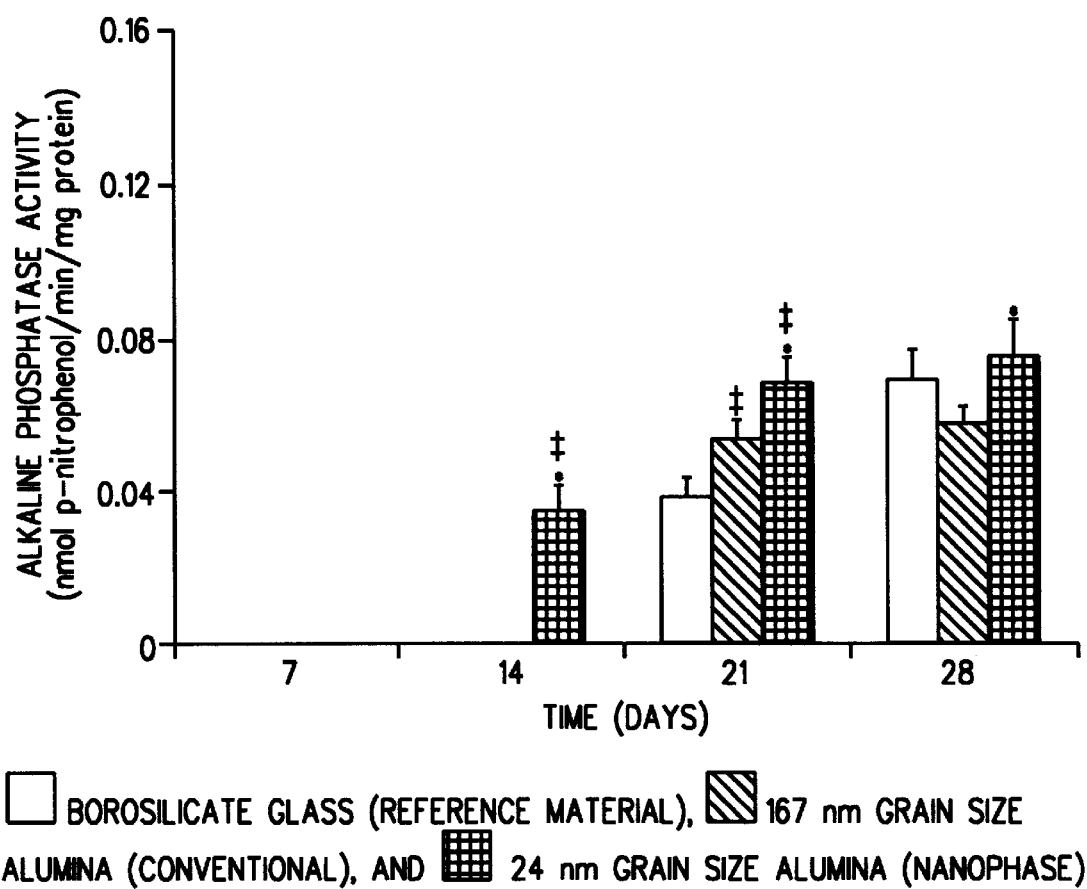
FIG. 9 is a graph showing alkaline phosphatase activity of osteoblasts seeded on (a) conventional and nanophase alumina; (b) conventional and nanophase titania; and (c) conventional and nanophase hydroxyapatite, each in comparison with a borosilicate glass reference.
Figure 9B:
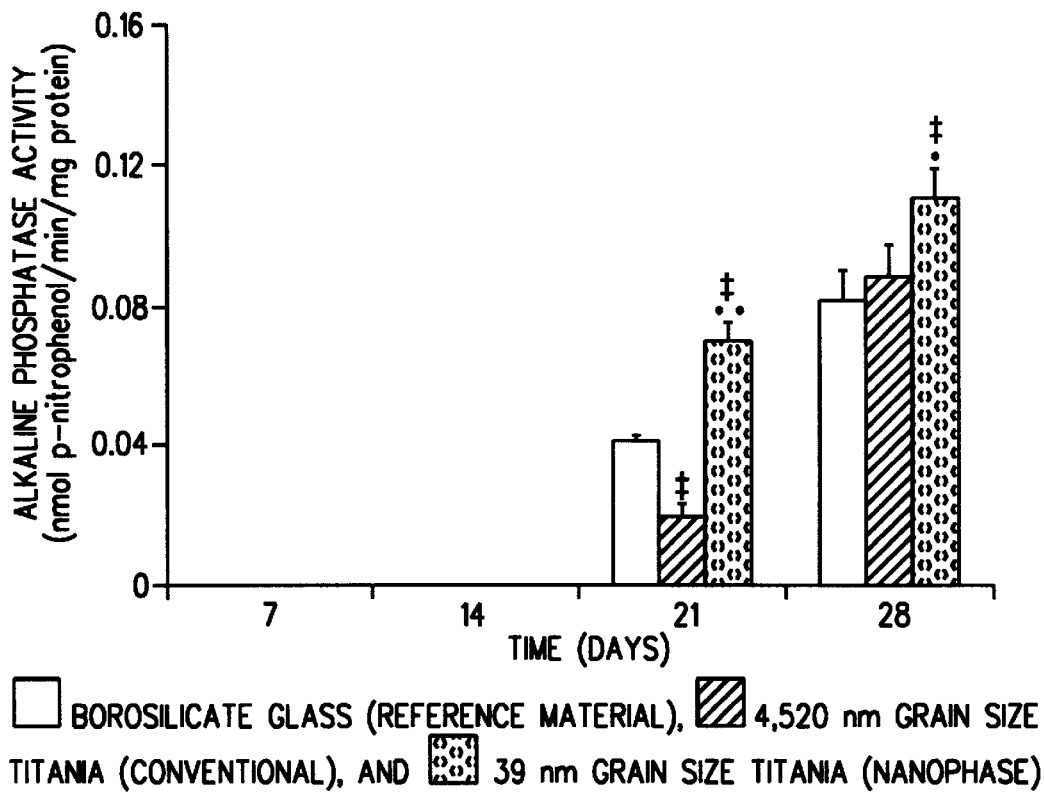
Figure 9C:
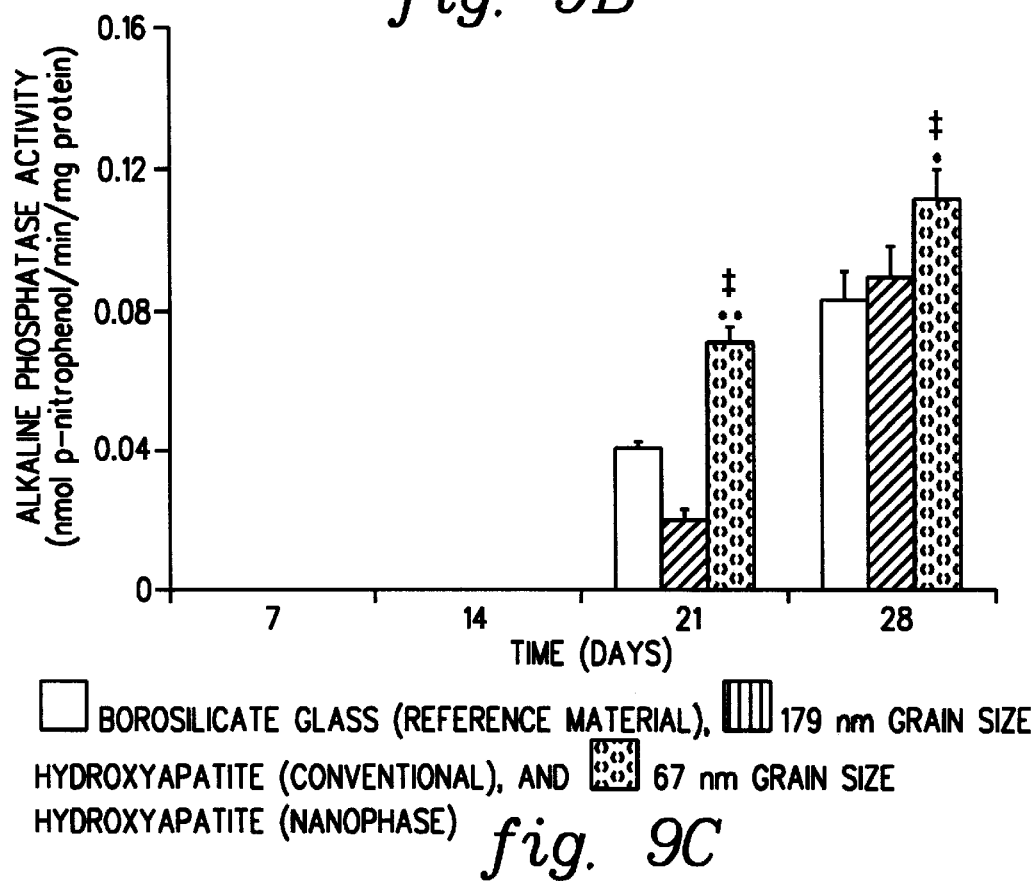

There were no detectable amounts of alkaline phosphatase activity by osteoblasts cultured on all substrates tested in the present study after 7 days and on titania, HA, and borosilicate glass after 14 days of culture. In contrast, alkaline phosphatase activity was significantly ($P<0.01$) greater on nanophase alumina after 14 days of culture. Alkaline phosphatase activity was also significantly ($P<0.01$) greater when osteoblasts were cultured on nanophase alumina, titania, and HA than on conventional formulations of the respective ceramics after 21 and 28 days of culture (FIGS. 9a, b, and c). Specifically at 28 days of culture, synthesis of alkaline phosphatase by osteoblasts on nanophase alumina, titania, and HA was 36, 22, and 37% greater than on conventional ceramic formulations, respectively. The highest ($P<0.01$) alkaline phosphatase activity was observed on nanophase titania (FIGS. 9a, b, and c).

Example 6
Deposition of Calcium in Extracellular Matrix

The substrates of interest to the present study, seeded either with or without osteoblasts (40,000 cells/cm$^2$), were cultured in DMEM (supplemented with 10% fetal bovine serum, 50 µg mL L-ascorbate (Σ) and 10 mM β-glycerophosphate (Σ)) under standard cell culture conditions for 7, 14, 21, and 28 days. At that time, cells were lysed as described above. The extracellular matrix of each preparation of interest to the present study was treated with 0.6 N HCl at 37° C. overnight. After the prescribed time period, the amount of calcium present in the acidic supernatant was spectrophotometrically quantified using a commercially available kit (Calcium Quantification Kit #587-A; Σ) and following manufacturer's instructions; light adsorbance of the samples was measured spectrophotometrically at 575 nm. Total calcium (µg/dL) was calculated from standard curves of adsorbance versus known concentrations of calcium measured in parallel with the experimental samples. Calcium concentration values were normalized by total protein synthesis; finally, these results were reported as µg of calcium/mg protein. In the case of calcium deposited on HA substrates, calcium concentration from HA samples maintained in acellular conditions was subtracted from all experimental values.

Figure 10A:
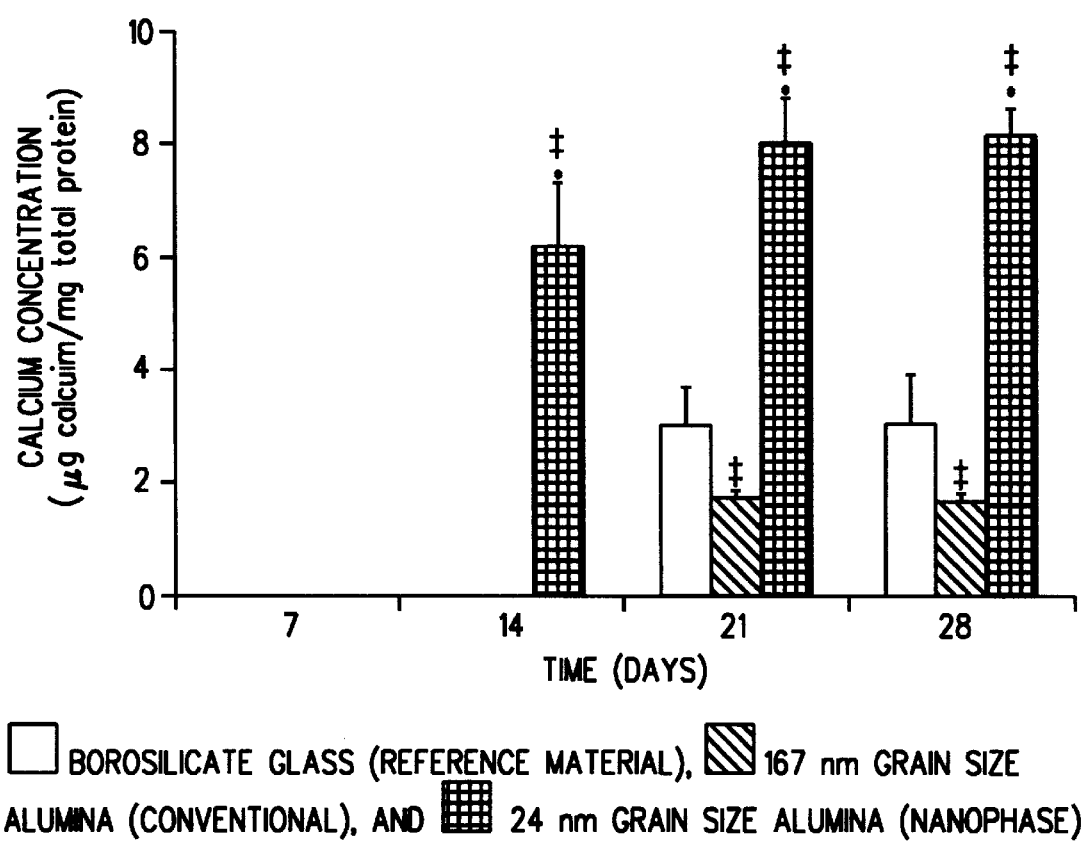
FIG. 10 is a graph showing extracellular calcium deposited by osteoblasts seeded on (a) conventional and nanophase alumina; (b) conventional and nanophase titania; and (c) conventional and nanophase hydroxyapatite, each in comparison with a borosilicate glass reference.
Figure 10B:
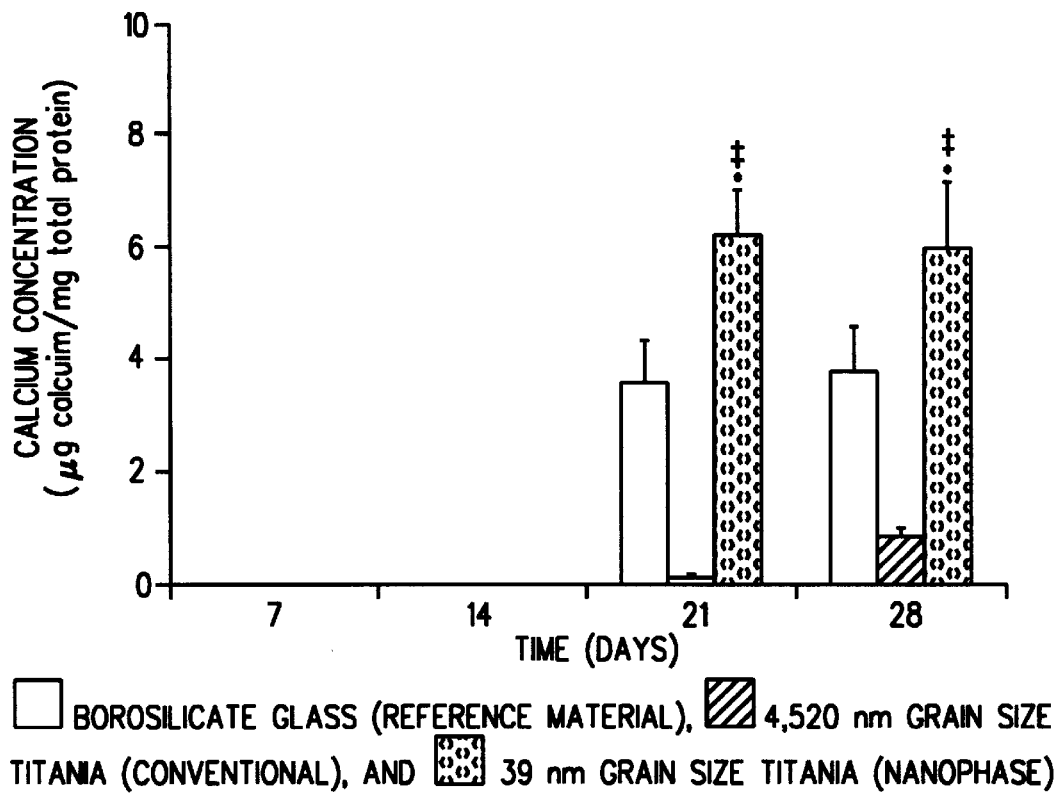
Figure 10C:
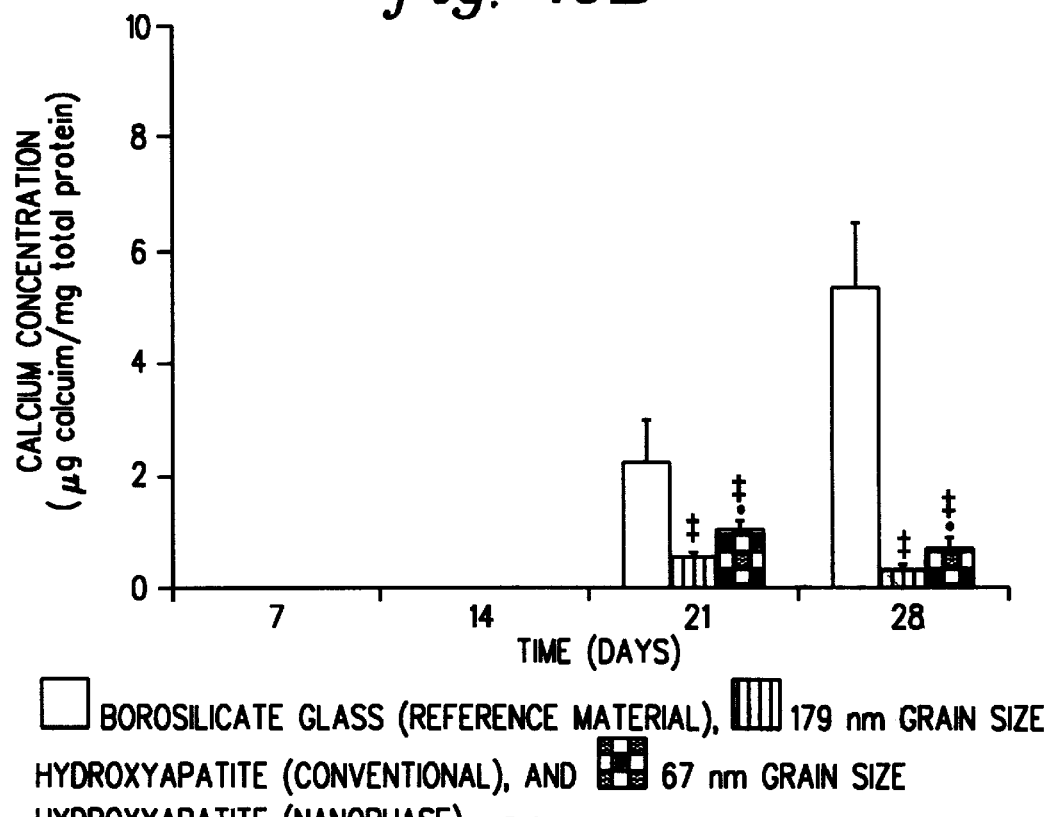

For any time period tested, there were no detectable amounts of calcium deposited on the substrates of interest to the present study cultured in an acellular environment (data not shown). In addition, there were no detectable amounts of calcium in the extracellular matrix after 7 days of osteoblast culture on any substrate tested in the present study (FIG. 10a, b, and c); after 14 days, calcium was only detected in the extracellular matrix of osteoblasts cultured on nanophase alumina. Calcium content in the extracellular matrix on all nanophase ceramics tested in the present study was significantly ($P<0.01$) greater than on respective conventional ceramic formulations after 21 and 28 days of culture (FIG. 10a, b, and c); specifically, after 28 days, the content of calcium in the extracellular matrix of osteoblasts cultured on nanophase alumina, titania, and HA was 4, 6, and 2 times greater than on respective conventional ceramics. Moreover, compared to nanophase HA, the calcium content in the extracellular matrix was significantly ($P<0.01$) greater after 28 days of cell culture on nanophase alumina and titania; calcium content was similar on nanophase alumina and titania during this time interval (FIGS. 10a, b, and c).

Example 7
Polylactic Acid: Nanophase Alumina Composites

Nanophase alumina/polylactic acid (PLA) composites with various weight percent (10, 20, and 30% nanophase alumina) loadings were prepared using modifications of published techniques. Briefly, PLA pellets were dissolved in chloroform, mixed with a nanophase alumina powder (23 nm size), cast and dried at room temperature for 48 hours. Homogeneous (100%) alumina compacts of 23 nm grain size were prepared as above. All samples were degreased, ultrasonically cleaned and sterilized according to standard procedures.

Adhesion of osteoblasts was measured using the same procedures as above. It was found that osteoblast adhesion on the composites increased with increasing content of alumina.

What is claimed is:

1. A method for enhancing osteoblast functions on a surface of an orthopaedic/dental implant comprising:

providing an orthopaedic/dental implant comprising one or more nanostructured ceramic having a grain size of 1–100 nm or a nanocomposite of one or more nanostructured ceramic having a grain size of 1–100 nm and at least one of an adhesion-promoting peptide and a non-peptide polymer, and exposing said orthopaedic/dental implant to osteoblast cells.

2. A method according to claim 1 wherein said orthopaedic/dental implant comprises one or more nanostructured ceramic chosen from alumina, titania, and hydroxyapatite.

3. A method according to claim 1 wherein said orthopaedic/dental implant comprises a nanocomposite comprising one or more nanostructured ceramic having a grain size of 1–100 nm and at least one of an adhesion-promoting peptide and a non-peptide polymer.

4. A method for enhancing osseointegration of an orthopaedic/dental implant comprising:

providing an orthopaedic/dental implant comprising one or more nanostructured ceramic having a grain size of 1–100 nm or a nanocomposite comprising one or more nanostructured ceramic having a grain size of 1–100 nm and at least one of an adhesion-promoting peptide and a non-peptide polymer, and placing said orthopaedic/dental implant in an animal.

5. A method according to claim 4 wherein said orthopaedic/dental implant comprises one or more nanostructured ceramic chosen from alumina, titania, and hydroxyapatite.

6. A method according to claim 4 wherein said orthopaedic/dental implant comprises a nanocomposite of one or more nanostructured ceramic having a grain size of 1–100 nm and at least one of an adhesion-promoting peptide and a non-peptide polymer.

7. An orthopaedic/dental implant consisting essentially of one or more nanostructured ceramics having a grain size of 1–100 nm and selected from the group consisting of alumina, titania and combinations thereof.

8. An orthopaedic/dental implant according to claim 7, wherein said one or more nanostructured ceramic is alumina.

9. An orthopaedic/dental implant according to claim 7, wherein said one or more nanostructured ceramic is titania.

10. An orthopaedic/dental implant according to claim 7 consisting essentially of one or more nanostructured ceramic having a grain size of about 30–70 nm.

11. An orthopaedic/dental implant according to claim 7 consisting essentially of alumina having a grain size of about 49–67 nm.

12. An orthopaedic/dental implant according to claim 7 consisting essentially of titania having a grain size of about 32–56 nm.

13. An orthopaedic/dental implant according to claim 7 comprising a substrate coated with said one or more nanostructured ceramic.

14. An orthopaedic/dental implant comprising a nanocomposite of one or more nanostructured ceramic having a grain size of 1–100 nm and at least one of an adhesion-promoting peptide and a non-peptide polymer.

15. An orthopaedic/dental implant according to claim 14 wherein said nanocomposite comprises one or more nanostructured ceramic having a grain size of 1–100 nm and one or more adhesion-promoting peptides.

16. An orthopaedic/dental implant according to claim 14 wherein said nanocomposite comprises one or more nanostructured ceramic having a grain size of 1–100 nm and one or more non-peptide polymers.

17. An orthopaedic/dental implant according to claim 14 wherein said one or more adhesion-promoting peptides is a peptide incorporating a KRSR or an RGD sequence.

18. An orthopaedic/dental implant according to claim 14, wherein said one or more non-peptide polymers is polylactic acid.

19. An orthopaedic/dental implant according to claim 14 comprising one or more nanostructured ceramic and polylactic acid.

20. An orthopaedic/dental implant according to claim 14 comprising a substrate coated with said nanocomposite.

21. An orthopaedic/dental implant comprising one or more nanostructured ceramics having a grain size of 1–100 nm, and wherein said one or more nanostructured ceramics is other than an apatite.

22. An orthopaedic/dental implant according to claim 21, wherein said one or more nanostructured ceramics is selected from the group consisting of alumina and titania.

* * * * *